(12) United States Patent
Lenox (10) Patent No.: US 11,752,309 B2
(45) Date of Patent: Sep. 12, 2023

(54) CATHETER DELIVERY GUIDEWIRE CLAMP

(71) Applicant: Mark Wayne Lenox, Idaho Falls, ID (US)

(72) Inventor: Mark Wayne Lenox, Idaho Falls, ID (US)

( * ) Notice: Subject to any disclaimer, the term of this patent is extended or adjusted under 35 U.S.C. 154(b) by 0 days.

(21) Appl. No.: 17/481,435

(22) Filed: Sep. 22, 2021

(65) Prior Publication Data

US 2023/0091819 A1    Mar. 23, 2023

(51) Int. Cl.
*A61M 25/09* (2006.01)
*A61M 39/06* (2006.01)
*A61M 25/01* (2006.01)

(52) U.S. Cl.
CPC ...... *A61M 25/09041* (2013.01); *A61M 39/06* (2013.01); *A61M 2025/0177* (2013.01); *A61M 2039/062* (2013.01); *A61M 2205/3331* (2013.01)

(58) Field of Classification Search
CPC ........ A61M 25/09041; A61M 25/0169; A61M 2025/0177; A61M 2025/0183; A61M 2025/0681; A61M 39/28; A61M 39/281; A61M 39/283–288
See application file for complete search history.

(56) References Cited

U.S. PATENT DOCUMENTS

| | | | | |
|---|---|---|---|---|
| 4,787,406 A * | 11/1988 | Edwards | ............. | A61M 39/283 251/8 |
| 5,203,056 A * | 4/1993 | Funk | ................... | A61M 39/284 251/10 |
| 6,843,779 B1 * | 1/2005 | Andrysiak | .......... | A61M 1/3403 604/5.01 |
| 8,206,283 B2 * | 6/2012 | Windheuser | .......... | A61M 25/02 600/104 |

(Continued)

FOREIGN PATENT DOCUMENTS

WO    WO-2014115336 A1 *   7/2014    ........ A61M 25/0169

OTHER PUBLICATIONS

Machine English Translation of WO 2014/115336, "WO2014115336A1 Replacement Assist Device, Guiding Catheter Assembly, and Guiding Catheter", Accessed from Espacenet on Jan. 14, 2022. (Year: 2014).*

*Primary Examiner* — Amber R Stiles
*Assistant Examiner* — Leah J Swanson
(74) *Attorney, Agent, or Firm* — Talem IP Law, LLP (57) ABSTRACT

A catheter delivery device includes a hollow longitudinal body, a fluidic bypass, and a hemostasis valve. The hollow longitudinal body includes a clamping portion and a guide catheter. The guide catheter has a distal end for access into a vessel of a patient and a proximal end coupled to the clamping portion. The clamping portion has a distal end coupled to the guide catheter, a proximal end coupled to the hemostasis valve, and a guidewire securing section. When (Continued)

the guidewire securing section of the clamping portion is securing the guidewire, the fluidic bypass maintains fluid communication between the guide catheter and the hemostasis valve. In some cases, the guidewire securing section and the fluidic bypass are separated by material within the hollow longitudinal body. In some cases, the fluidic bypass is separate from the guidewire securing section outside of the hollow longitudinal body.

14 Claims, 6 Drawing Sheets

(56) References Cited

U.S. PATENT DOCUMENTS

| | | | |
|---|---|---|---|
| 2003/0225379 A1* | 12/2003 | Schaffer | A61M 39/0613 |
| | | | 604/250 |
| 2014/0203555 A1* | 7/2014 | Frankland | A61M 25/09 |
| | | | 285/390 |
| 2014/0324026 A1* | 10/2014 | Chrisman | A61M 25/09041 |
| | | | 604/528 |

* cited by examiner

CATHETER DELIVERY GUIDEWIRE CLAMP

BACKGROUND

Percutaneous Coronary Interventions (PCIs) have become standard practice in the field of cardiology to treat occluded coronary vessels. During a PCI, a guide catheter is placed at the ostium of the coronary vessel to be treated. At the proximal end of the guide catheter (e.g., the portion that is external to the patient's vessel and skin), a hemostasis valve may be attached to control bleeding. A guidewire is then inserted through the guiding catheter and is directed down the coronary vessel through a lesion in the vessel until the tip of the guidewire is suitably past the lesion. Interventional catheter-based devices, such as balloons, stents, and/or imaging catheters, are then delivered over the guidewire to the lesion to treat the lesion and restore normal blood flow through the vessel.

Monorail/rapid exchange catheter systems are devices where the guidewire enters the catheter at the distal tip of the catheter, but remains within the body of the catheter for approximately 20 to 30 centimeters before the guidewire exits laterally through the side of the catheter. Numerous interventional and diagnostic device catheters such as balloons, stents, intravascular ultrasound catheters, etc. are available in a monorail/rapid exchange configuration. Monorail/rapid exchange device catheters require diligent care and attention during insertion and removal from the guiding catheter and hemostasis valve to avoid unintended guidewire movement. During insertion of the rapid exchange device catheter, assistance is required by an assistant to the primary operator (e.g., the physician) to "fix" or "hold" the guidewire so that the guidewire is not advanced further into the patient as the primary operator inserts the catheter through the hemostasis valve. Specifically, the assistant must hold the guidewire as the proximal tip of the catheter is inserted into the hemostasis valve and continue holding the wire until the guidewire exit of the rapid exchange section of the catheter is within the hemostasis valve. Once the proximal exit of the guidewire lumen is within the hemostasis valve, the primary operator can grasp and control the guidewire as the remainder of the catheter is advanced within the guiding catheter since the proximal portion of the guidewire is now external and parallel to the catheter.

During this procedure, if the coordination between the primary operator and the assistant is sub-optimal, there is risk of unintended guidewire movement. In a worst-case scenario, the distal tip of the guidewire could perforate the coronary vessel if the guidewire is allowed to advance unrestricted into the vessel. Removal of the device catheter from the guiding catheter and hemostasis valve is similarly complex and can result in unintended guidewire movement. Specifically, during the initial portion of device catheter removal, the primary operator has control of the guidewire up until the point where the proximal guidewire exit of the catheter emerges from the hemostasis valve. At this point, it becomes necessary for the primary operator to "walk the catheter back" for the length of the rapid exchange section of the device catheter. To remove the device catheter over this segment, the operator must grasp and securely hold the guidewire only a short distance proximal to the guidewire exit and then carefully retract the catheter out of the hemostasis valve in a stepwise fashion. The length of each retraction must be a short enough distance to prevent the guidewire from either moving or buckling during the device catheter retraction. If the guidewire buckles during a retraction, the result is the distal tip of the guidewire inadvertently being pulled back, which prolongs the procedure (e.g., because the distal tip of the guidewire must be re-positioned) and enhances risk to the patient (e.g., because the moving or buckling of a guidewire can damage the patient's vessel).

BRIEF SUMMARY

A catheter delivery guidewire clamp is described that can facilitate device catheter exchange during percutaneous coronary intervention using rapid exchange devices. A catheter delivery guidewire clamp as described in certain implementations herein provides the ability to secure a guidewire during insertion (and removal) of a device catheter in and through a hemostasis valve (e.g., eliminating or reducing the risk of unintended guidewire movement) while simultaneously maintaining fluidic pressure throughout the catheter delivery device and simplifying the insertion (and removal) of rapid exchange style device catheters. Advantageously, the catheter delivery guidewire clamp can be coupled between portions of existing catheter delivery devices (e.g., a guide catheter and a hemostasis valve) or manufactured as part of catheter delivery devices.

A catheter delivery device having a catheter delivery guidewire clamp can include a hollow longitudinal body, a fluidic bypass, and a hemostasis valve. The hollow longitudinal body includes a clamping portion and a guide catheter. The guide catheter has a distal end for access into a vessel of a patient and a proximal end coupled to the clamping portion. The clamping portion has a distal end coupled to the guide catheter, a proximal end coupled to the hemostasis valve, and a guidewire securing section. When the guidewire securing section of the clamping portion is securing the guidewire, the fluidic bypass maintains fluid communication between the guide catheter and the hemostasis valve. The hemostasis valve is coupled to the proximal end of the clamping portion.

A catheter delivery guidewire clamp for device catheter delivery can include a hollow longitudinal body having a distal end, a proximal end, and a guidewire securing section and a fluidic bypass. The guidewire securing section is configured to secure a guidewire while the fluidic bypass maintains fluid communication between the distal end and the proximal end. The guidewire securing section can include a clamp or be formed of deformable material that can itself be used as a clamp.

In some cases, the catheter delivery guidewire clamp further includes a guide catheter extending from the distal end of the guidewire securing section and the proximal end of the hollow longitudinal body is configured to couple to a hemostasis valve. In some cases, the catheter delivery guidewire clamp further includes a hemostasis valve extending from the proximal end of the guidewire securing section and the distal end of the hollow longitudinal body is configured to couple to a guide catheter.

A method of using a catheter delivery device can include inserting a distal end of a guide catheter of a catheter delivery device into a vessel of a patient; inserting a guidewire through the hemostasis valve and the hollow longitudinal body and into the vessel of the patient; securing the guidewire by clamping the guidewire securing section of the clamping portion; inserting a device catheter through the hemostasis valve and into the hollow longitudinal body; releasing the clamp guidewire securing section of the clamping portion; and inserting the catheter into the vessel of the patient.

When removing the device catheter, the method can include removing the device catheter from the vessel of the patient and into the hollow longitudinal body; securing the guidewire by clamping the guidewire securing section of the clamping portion; and removing the device catheter from the hollow longitudinal body and out of the hemostasis valve of the catheter delivery device.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

A catheter delivery guidewire clamp is described that can facilitate device catheter exchange during percutaneous coronary intervention using rapid exchange catheters. A catheter delivery guide-wire clamp as described in certain implementations herein provides the ability to secure a guidewire during insertion (and removal) of a device catheter in and through a hemostasis valve (e.g., eliminating the risk of unintended guidewire movement) while simultaneously maintaining fluidic pressure throughout the catheter delivery device and simplifying the insertion (and removal) of rapid exchange style catheters. Advantageously, the catheter delivery guidewire clamps can be coupled between portions of existing catheter delivery devices (e.g., a guide catheter and a hemostasis valve) or manufactured as part of catheter delivery devices.

Figure 1A:
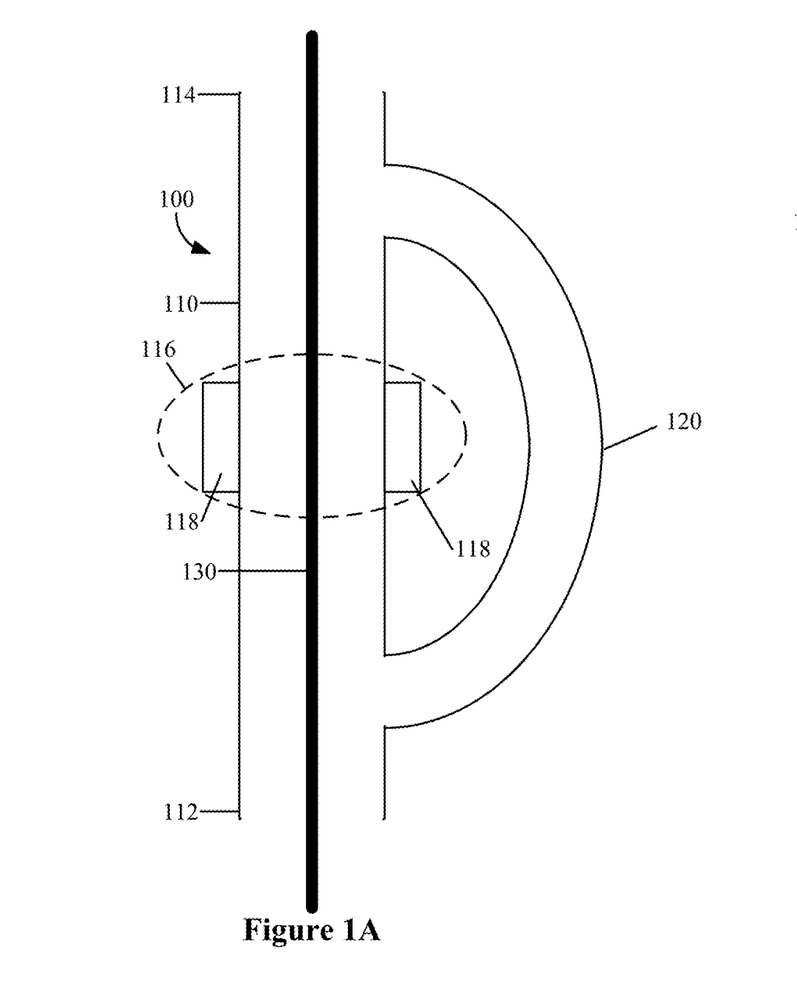
FIGS. 1A and 1B illustrate a longitudinal cross-section of a catheter delivery guidewire clamp for use in delivery of a device catheter to a vessel of a patient with an external fluidic bypass.
Figure 1B:
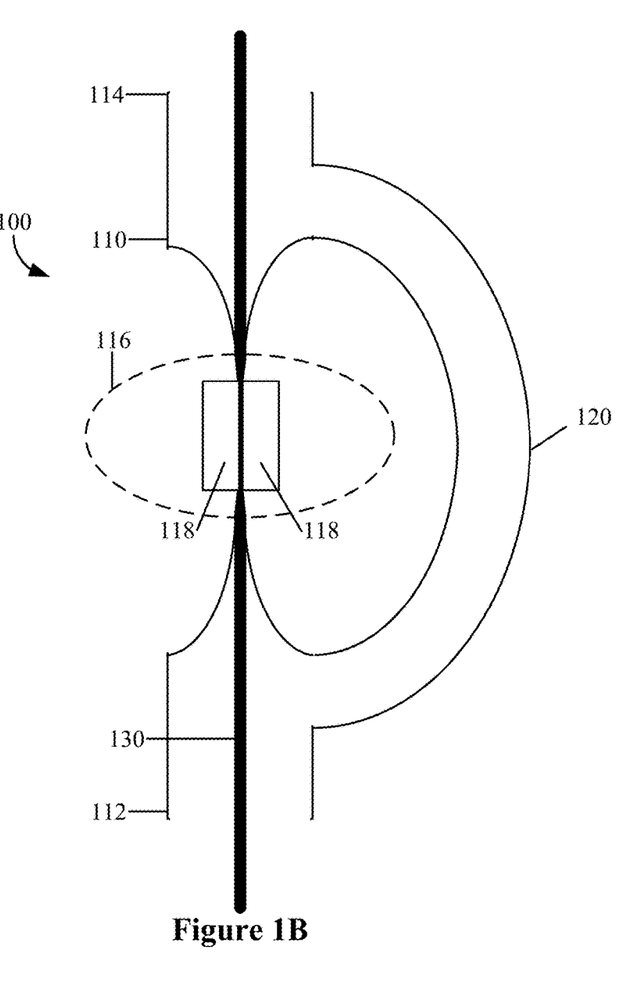

FIGS. 1A and 1B illustrate a longitudinal cross-section of a catheter delivery guidewire clamp for use in delivery of a device catheter to a vessel of a patient with an external fluidic bypass. Referring to FIG. 1A, a catheter delivery guidewire clamp 100 includes a hollow longitudinal body 110 and a fluidic bypass 120. The hollow longitudinal body 110 includes a distal end 114, a proximal end 112, and a guidewire securing section 116. Here, the guidewire securing section 116 of the hollow longitudinal body 110 is in an open position. An open position allows for the movement of a guidewire 130 and/or fluid (e.g., blood).

Referring to FIG. 1B, the guidewire securing section 116 of the hollow longitudinal body 110 is shown in a closed position. In the closed position, the guidewire 130 is secured and/or immobilized and movement of fluid is restricted between the distal end 114 and the proximal end 112 through the guidewire securing section 116. However, even when the guidewire securing section 116 is in the closed position, the fluidic bypass 120 maintains fluidic communication between the distal end 114 of the hollow longitudinal body 110 and the proximal end 112 of the hollow longitudinal body 110.

As illustrated in FIGS. 1A and 1B, the fluidic bypass 120 is separate from the guidewire securing section 116 outside of the hollow longitudinal body 110 and is coupled to the distal end 114 of the hollow longitudinal body 110 and the proximal end 112 of the hollow longitudinal body 110. The guidewire securing section 116 has a closed position and an open position. In some cases, the guidewire securing section 116 is placed in the closed position by a clamp 118 included in the guidewire securing section 116. In other words, the clamp 118 may be included within and/or coupled to the guidewire securing section 116 during manufacture of the catheter delivery guidewire clamp 100. In some cases, the guidewire securing section 116 is placed in the closed position by an external force (e.g., an external clamp and/or a user pinching the guidewire securing section 116 with their hand). In some cases, the guidewire securing section 116 is deformable such that the material of the guidewire securing section 116 can itself be used as a clamp.

In some cases, the catheter delivery guidewire clamp 100 further includes a guide catheter extending from the distal end 114 of the hollow longitudinal body 110 and the proximal end 112 is configured to couple to a hemostasis valve. For example, the proximal end 112 may include a threaded attachment, a nut and bolt attachment, a hook-and-loop attachment, a tongue-and-groove attachment, button-type attachment, quick-snap attachment, or the like for coupling to a hemostasis valve. In some cases, the catheter delivery guidewire clamp 100 further includes a hemostasis valve extending from the proximal end 112 of the hollow longitudinal body 110 and the distal end 114 is configured to couple to a guide catheter. For example, the distal end 114 may include a threaded attachment, a nut and bolt attachment, a hook-and-loop attachment, a tongue-and-groove attachment, button-type attachment, quick-snap attachment, and or like for coupling to a guide catheter.

Figure 2A:
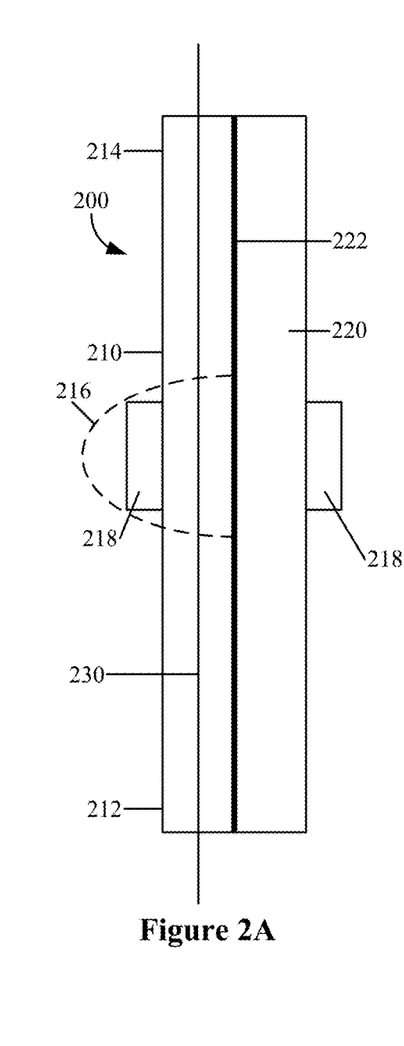
FIGS. 2A and 2B illustrate a longitudinal cross-section of a catheter delivery guidewire clamp for use in delivery of a device catheter to a vessel of a patient with an internal fluidic bypass.
Figure 2B:
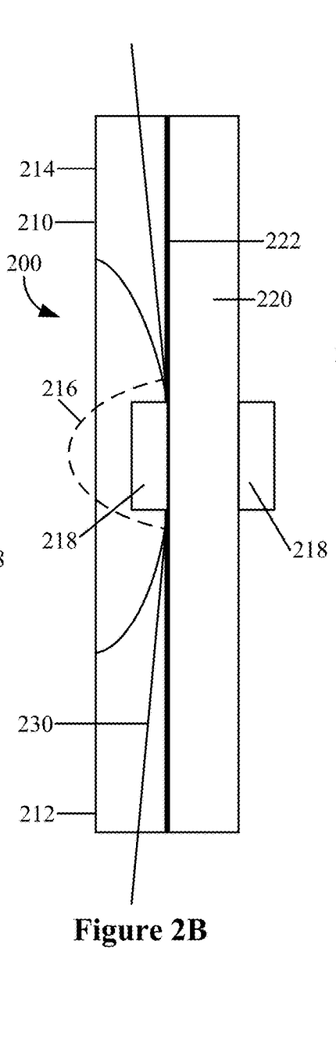
Figure 2C:
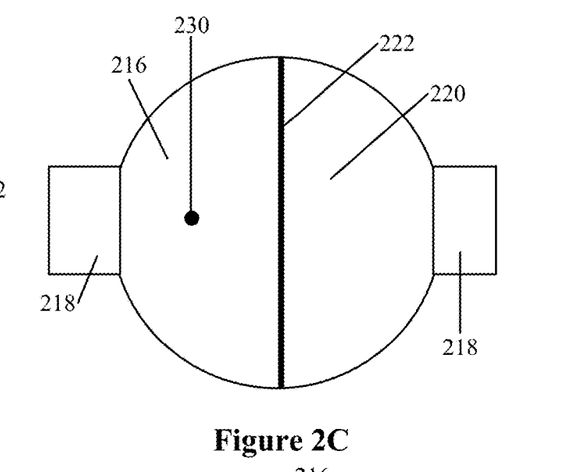
FIGS. 2C and 2D illustrate a lateral cross-section at a guidewire securing section of a catheter delivery guidewire clamp for use in delivery of a device catheter to a vessel with an internal fluidic bypass.
Figure 2D:
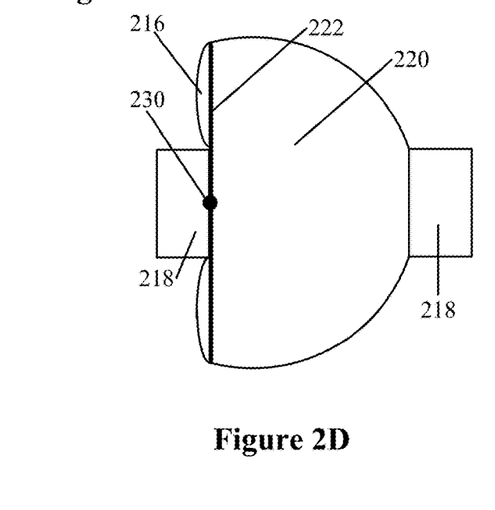

FIGS. 2A and 2B illustrate a longitudinal cross-section of a catheter delivery guidewire clamp for use in delivery of a device catheter to a vessel of a patient with an internal fluidic bypass. FIGS. 2C and 2D illustrate a lateral cross-section at a guidewire securing section of a catheter delivery guidewire clamp for use in delivery of a device catheter to a vessel with an internal fluidic bypass. FIG. 2C is the lateral cross-section at the guidewire securing section of the catheter delivery guidewire clamp shown in FIG. 2A. FIG. 2D is the lateral cross-section at the guidewire securing section of the catheter delivery guidewire clamp shown in FIG. 2B. Referring to FIGS. 2A and 2C, a catheter delivery guidewire clamp 200 includes a hollow longitudinal body 210 and a fluidic bypass 220. The hollow longitudinal body 210 includes a proximal end 212, a distal end 214, and a guidewire securing section 216. In this case, the guidewire securing section 216 of the hollow longitudinal body 210 is in an open position. As can be seen in FIG. 2C, the guidewire 230 is not secured and/or immobilized within the guidewire securing section 216.

Referring to FIGS. 2B and 2D, the guidewire securing section 216 of the hollow longitudinal body 210 is in a closed position. In the closed position, the guidewire 230 is secured and/or immobilized and movement of fluid is restricted between the proximal end 212 and the distal end 214 through the guidewire securing section 216. However, even when the guidewire securing section 216 is in the closed position, the fluidic bypass 220 maintains fluidic communication between the proximal end 212 of the hollow longitudinal body 210 and the distal end 214 of the hollow longitudinal body 210. As can be seen in FIG. 2D, the guidewire 230 is secured and/or immobilized within the guidewire securing section 216.

As illustrated in FIGS. 2A-2D, the guidewire securing section 216 and the fluidic bypass 220 are separated by material 222 within the hollow longitudinal body 210. In some cases, the material 222 and/or the fluidic bypass 220 are made of (relatively) non-deformable material such that a force from a clamp will cause (relatively) no deformation of the material 222 and/or the fluidic bypass 220. In some cases, the guidewire securing section 216 of the hollow longitudinal body 210 is deformable such that the guidewire securing section 216 secures and/or immobilizes the guidewire 230 by a clamp 218 and/or person tightening the deformable material against the material 222 within the hollow longitudinal body 210. In some cases, the clamp 218 is included in the guidewire securing section 216. In some cases, the clamp 218 is external (e.g., separate from) the guidewire securing section 216. In some cases, the clamp 218 is one of a spring clamp, a vice clamp, a one-handed bar clamp, a power clamp, a trigger clamp, a screw clamp, a clip hanger clamp, a hose clamp, a medical clamp, a Foerster clamp, and a hemostatic clamp. In some cases, the clamp 218 may be an internal clamp that is similar to a valve (e.g., a gate valve, globe valve, a pinch valve, a butterfly valve, or the like) that is used to secure the guidewire 230 within the guidewire securing section 216. In some cases, the clamp 218 may be an internal clamp that is similar to a medical balloon (e.g., and could even be filled electropneumatically) that is used to secure the guidewire 230 within the guidewire securing section 216.

Figure 3A:
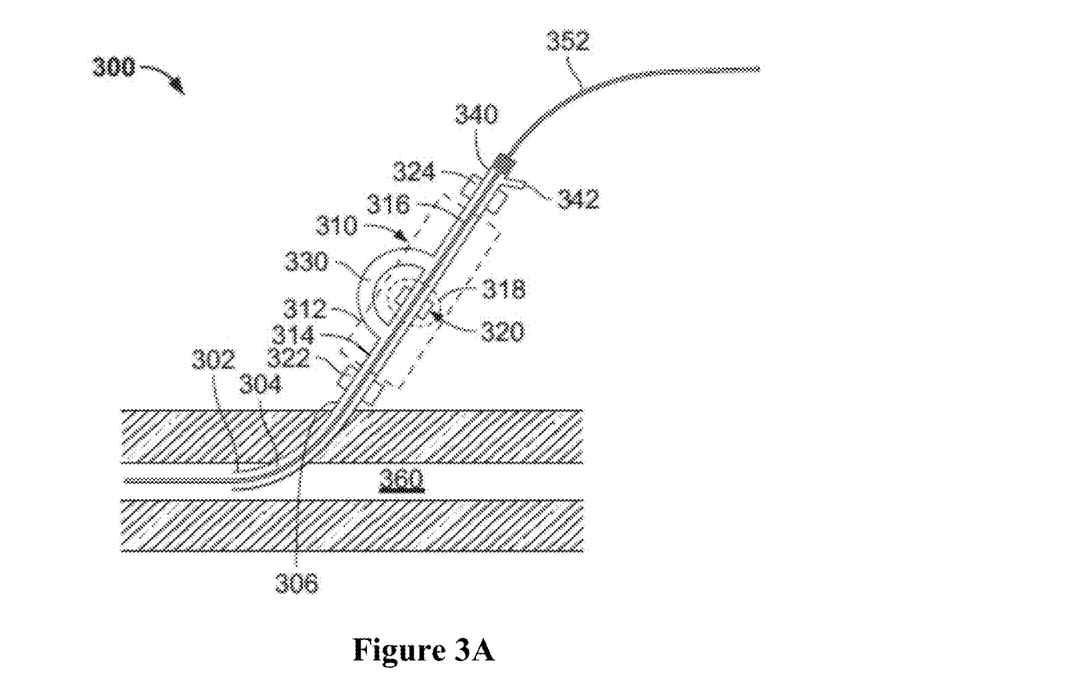
FIGS. 3A-3D illustrate a catheter delivery device delivering a catheter to a vessel of a patient.
Figure 3B:
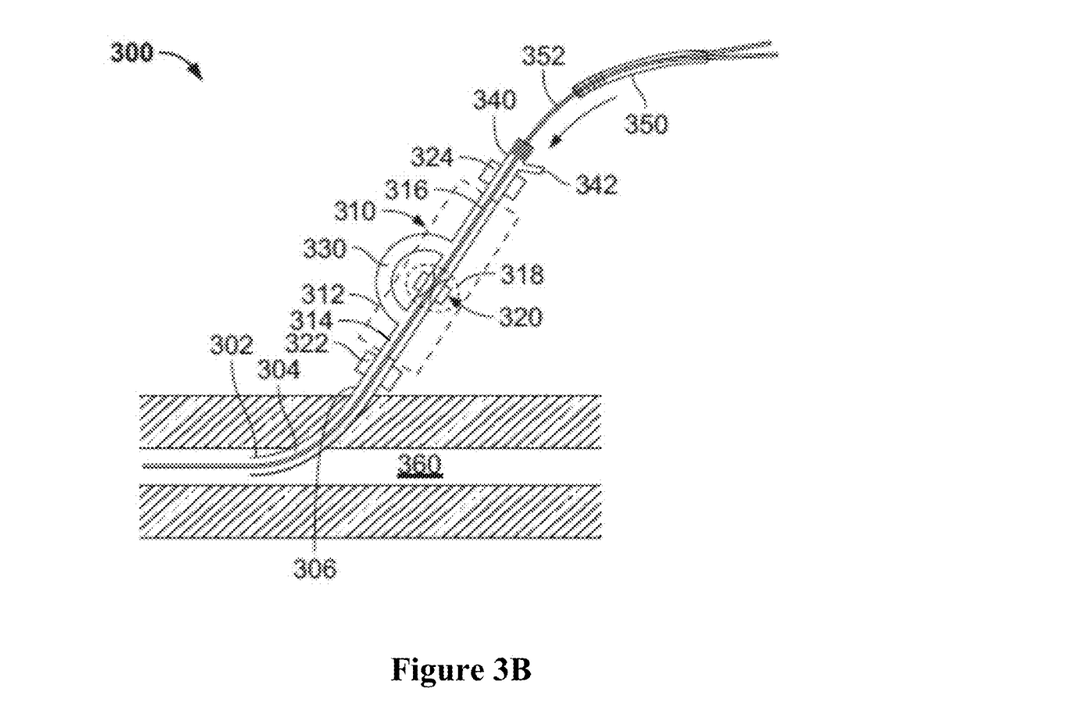
Figure 3C:
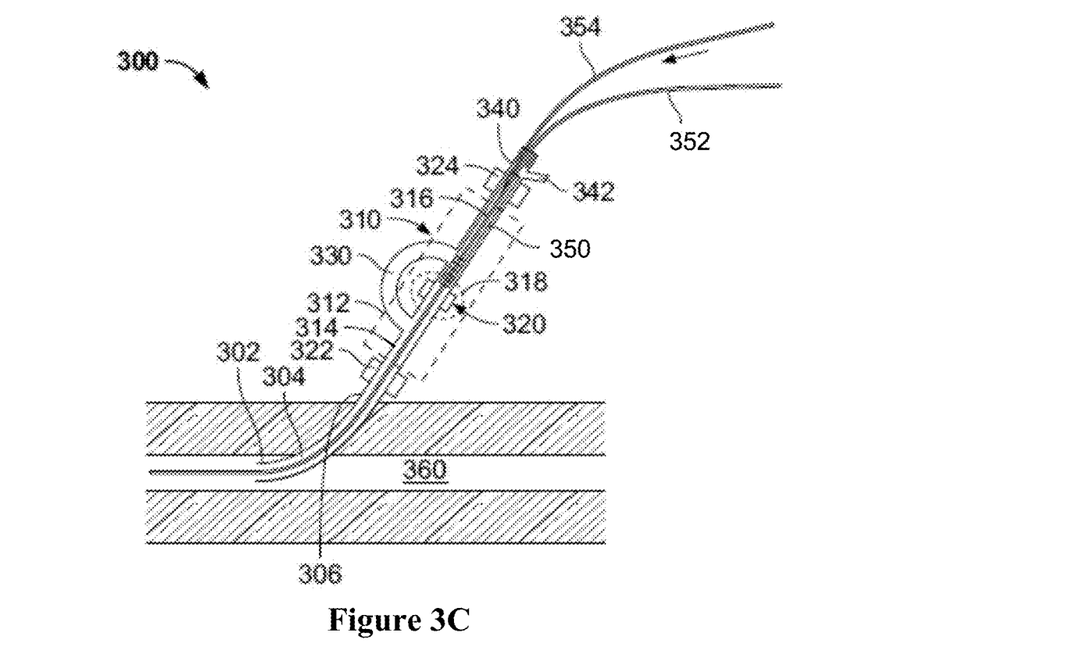
Figure 3D:
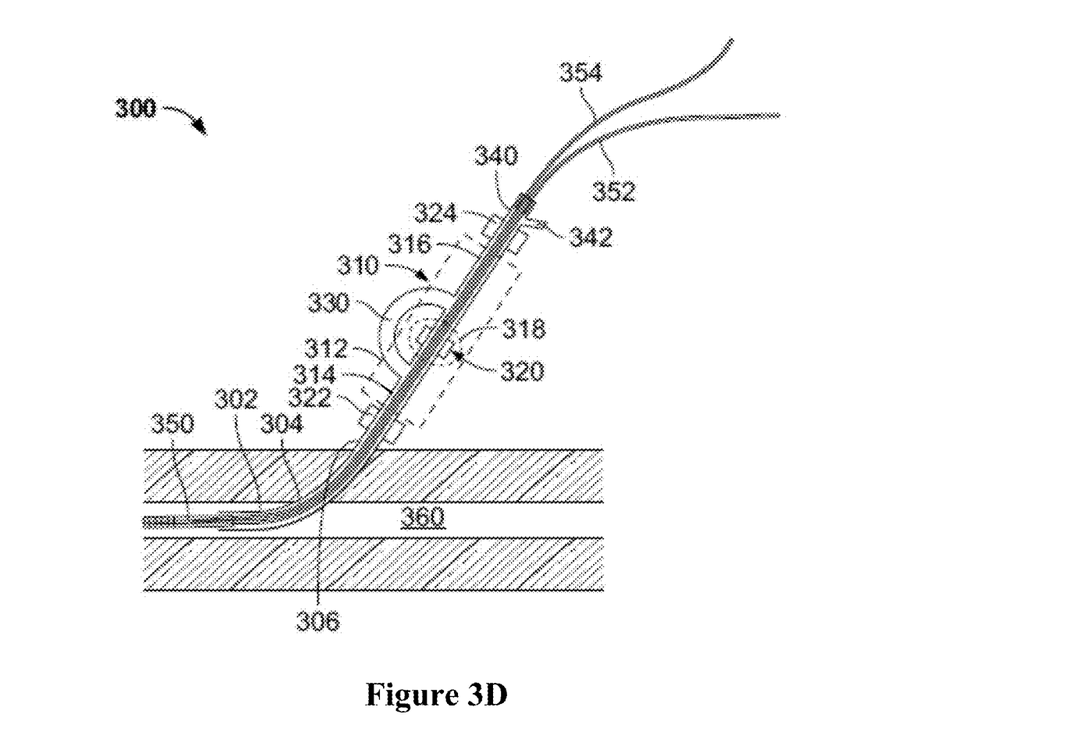
Figure 4A:
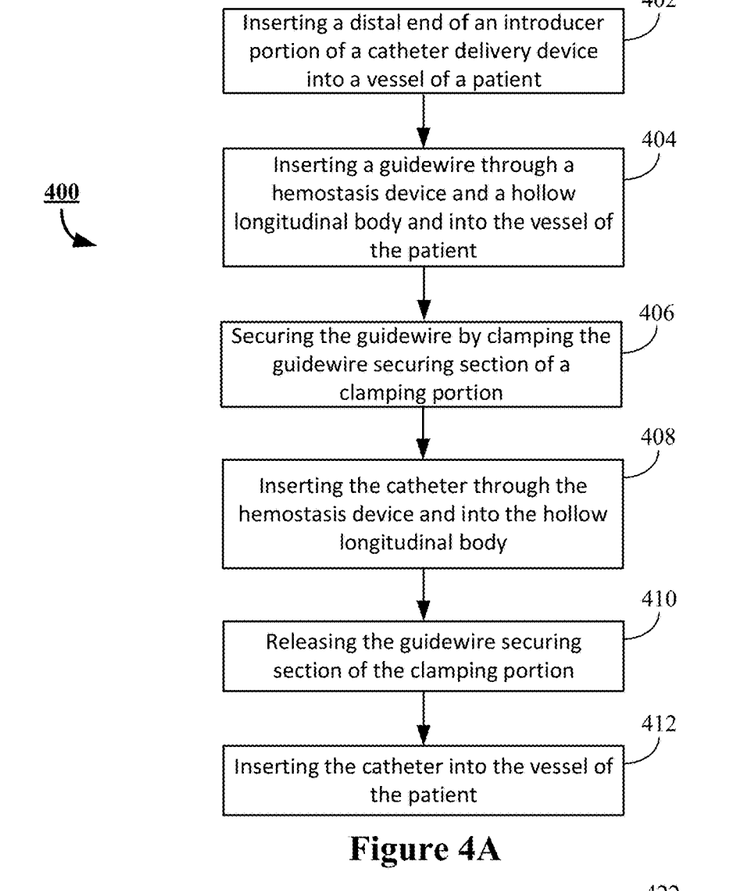
FIG. 4A illustrates a method of using a catheter delivery device to deliver a device catheter to a vessel of a patient.

FIG. 3A-3D illustrate a catheter delivery device delivering a device catheter to a vessel of a patient; and FIG. 4A illustrates a method of using a catheter delivery device to deliver a catheter to a vessel of a patient.

As illustrated in FIGS. 3A-3D, a catheter delivery device 300 having a catheter delivery guidewire clamp includes a hollow longitudinal body 310, an external fluidic bypass 330, and a hemostasis valve 340. The hollow longitudinal body 310 includes a guide catheter 304 and a clamping portion 312. The guide catheter 304 includes a distal end 302 for accessing the vessel 360 of the patient and a proximal end 306 coupled to the clamping portion 312. The clamping portion 312 includes a distal end 314 coupled to the guide catheter 304, a proximal end 316 coupled to the hemostasis valve 340, and a guidewire securing section 318. The hemostasis valve 340 is coupled to the proximal end 316 of the clamping portion 312.

In some cases, the hemostasis valve 340 includes pressure monitor port 342. In some cases, the catheter delivery device 300 includes attachment mechanism 322 to attach the proximal end 306 of the guide catheter 304 to the distal end 314 of the clamping portion 312. In some cases, attachment mechanism 322 is not included and the guide catheter 304 is instead formed to and/or extending from the clamping portion 312 (e.g., during manufacturing). In some cases, the catheter delivery device 300 includes attachment mechanism 324 to attach the proximal end 316 of the clamping portion 312 to the hemostasis valve 340. In some cases, no attachment mechanism 324 is included and the hemostasis valve 340 is formed to and/or extending from the clamping portion 312 (e.g., during manufacturing). In some cases, one or both the attachment mechanisms 322, 324 are a threaded attachment, a nut and bolt attachment, a hook-and-loop attachment, a tongue-and-groove attachment, button-type attachment, quick-snap attachment, or the like for respectively coupling to the guide catheter 304 and/or hemostasis valve 340.

Referring to FIG. 3B and FIG. 4A, a method 400 of using the catheter delivery device 300 to deliver a device catheter 350 to a vessel 360 of a patient includes inserting (402) the distal end 302 of the guide catheter 304 of the catheter delivery device 300 into the vessel 360 of the patient.

The method 400 further includes inserting (404) a guidewire 352 through the hemostasis valve 340 and the hollow longitudinal body 310 (thence through the guide catheter 304) and into the vessel 360 of the patient. In some cases, inserting (404) the guidewire 352 into the vessel 360 of the patient includes positioning the guidewire to a desired location within the vessel 360 of the patient.

Referring to FIG. 3B and FIG. 4A, the method 400 further includes securing (406) the guidewire 352 by clamping (e.g., via clamp 320) the guidewire securing section 318 of the clamping portion 312 (e.g., guidewire securing section 318 is in the closed position) and inserting (408) the device catheter 350 through the hemostasis valve 340 and into the hollow longitudinal body 310. When the guidewire securing section 318 of the clamping portion 312 is securing the guidewire 352 (e.g., as illustrated in FIG. 3B), the fluidic bypass 330 maintains fluid communication between the guide catheter 304 and the hemostasis valve 340. Indeed, while clamping the guidewire securing section 318 of the clamping portion 312 occludes the primary pathway for the fluids (e.g., blood), the fluidic bypass 330 allows hemodynamic pressure information to pass around the guidewire securing section 318 to the pressure monitor port 342. The fluidic bypass 330 also allows for blood flow around the guidewire securing section 318, preventing unintended air ingress through the hemostasis valve 340 (which can create an air embolus). Furthermore, by securing (406) the guidewire 352, coordination between the primary operator and the assistant becomes less critical and may no longer be needed.

Referring to FIG. 3C and FIG. 4A, the method 400 further includes releasing (410) the guidewire securing section 318 of the clamping portion 312 (e.g., guidewire securing section 318 is in the open position). In some cases, the guidewire securing section 318 of the clamping portion 312 is released when the device catheter 350 reaches the guidewire securing section 318. In some cases, the guidewire securing section 318 of the clamping portion 312 is released by releasing and/or removing a clamp 320. In other cases (e.g., when clamp 320 is not used), the guidewire securing section 318 of the clamping portion 312 is released by a user releasing the guidewire securing section 318 with their hand/fingers. Referring to FIG. 3D and FIG. 4A, the method 400 further includes inserting (412) the device catheter 350 into the vessel 360 of the patient. That is, once the device catheter 350 passes through the hemostasis valve 340, the guidewire securing section 318 can be released to enable the device catheter 350 to pass through the guidewire securing section 318 and be inserted into the vessel 360.

Figure 4B:
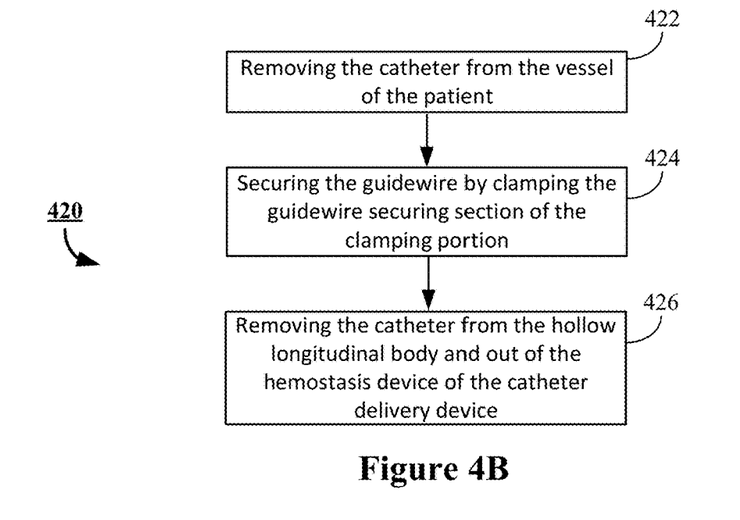
FIG. 4B illustrates a method of using a catheter delivery device to remove a device catheter from a vessel of a patient.

FIG. 4B illustrates a method of using a catheter delivery device to remove a device catheter from a vessel of a patient.

Referring to FIG. 4B, the method 420 includes removing (422) the device catheter 350 from the vessel 360 of the patient and into the hollow longitudinal body 310, securing (424) the guidewire 352 by clamping the guidewire securing section 318 of the clamping portion 312, and removing (426) the device catheter 350 from the hollow longitudinal body 310 and out of the hemostasis valve 340 of the catheter delivery device 300. Similar to the method 400 of insertion, the fluidic bypass 330 maintains fluid communication between the guide catheter 304 and the hemostasis valve 340 even when the guidewire 352 is secured (424) in the guidewire securing section 318. A tether (e.g., body 354 of device catheter 350 of FIGS. 3C and 3D) can be used to remove (422, 426) the catheter 350 from of the vessel 360 and the device 300. The guidewire 352 can be secured (424) once the device catheter 350 is past the guidewire securing section 318.

Figure 5A:
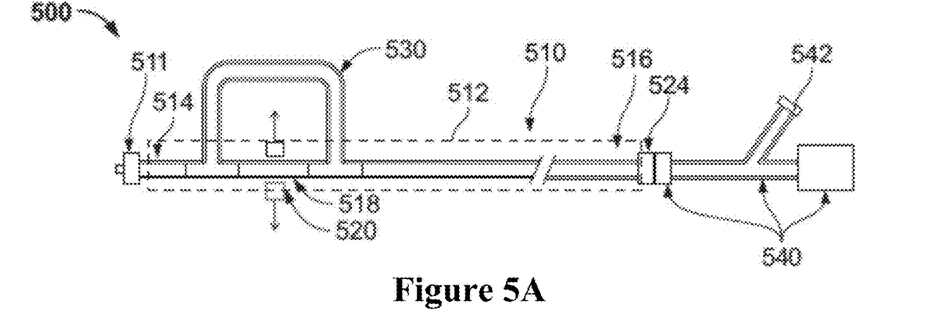
FIGS. 5A and 5B illustrate a catheter delivery device for use in delivery of a device catheter to a vessel of a patient with an external fluidic bypass.
Figure 5B:
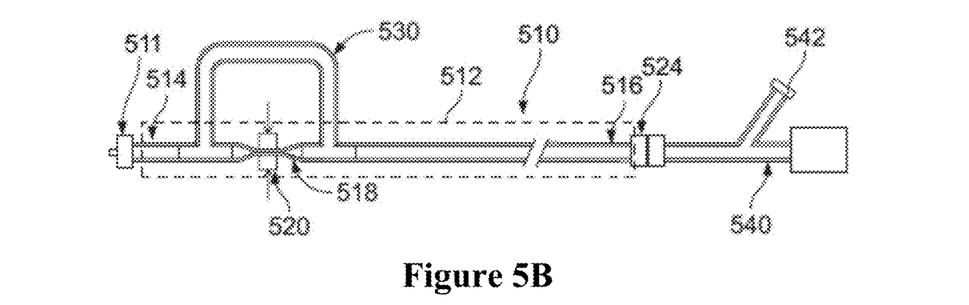

FIGS. 5A and 5B illustrate a catheter delivery device for use in delivery of a catheter to a vessel of a patient with an external fluidic bypass. Device 500 may be used to carry out the methods 400 and 420 described in FIGS. 4A and 4B. Referring to FIGS. 5A and 5B, a catheter delivery device 500 includes a hollow longitudinal body 510, an external fluidic bypass 530, and a hemostasis valve 540. The hollow longitudinal body 510 includes a clamping portion 512 and is configured to couple to a guide catheter (e.g., via attachment 511). For example, the attachment 511 may be a threaded attachment, a nut and bolt attachment, a hook-and-loop attachment, a tongue-and-groove attachment, button-type attachment, quick-snap attachment, or the like for coupling to a guide catheter. The clamping portion 512 includes a distal end 514 coupled to the attachment 511, a proximal end 516 coupled to the hemostasis valve 540 (e.g., via attachment mechanism 524), and a guidewire securing section 518. As with attachment 511, attachment mechanism 524 can be a threaded attachment, a nut and bolt attachment, a hook-and-loop attachment, a tongue-and-groove attachment, button-type attachment, quick-snap attachment, or the like for coupling to the hemostasis valve 540. In some cases, the hemostasis valve includes a pressure monitor port 542. In addition, in this example, the guidewire securing section 518 includes a clamp 520. It should be noted that FIG. 5A illustrates the clamp 520 in the open position; in FIG. 5B, the clamp 520 is in the closed position.

Figure 6A:
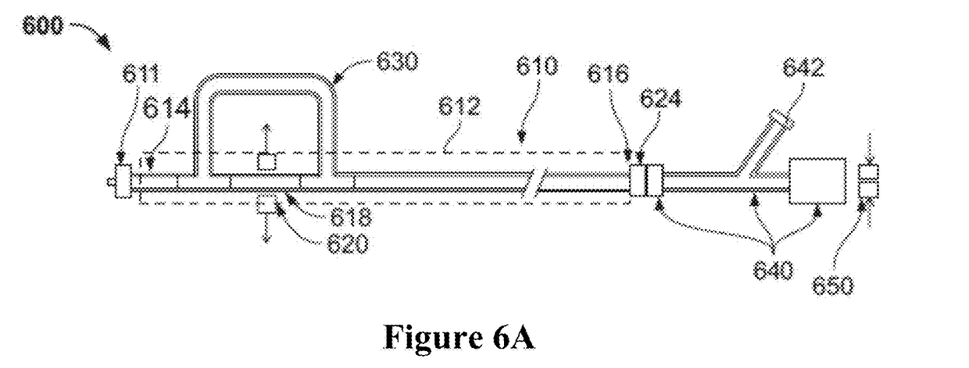
FIGS. 6A and 6B illustrate a catheter delivery device with an external clamp for use in delivery of a device catheter to a vessel of a patient with an external fluidic bypass.
Figure 6B:
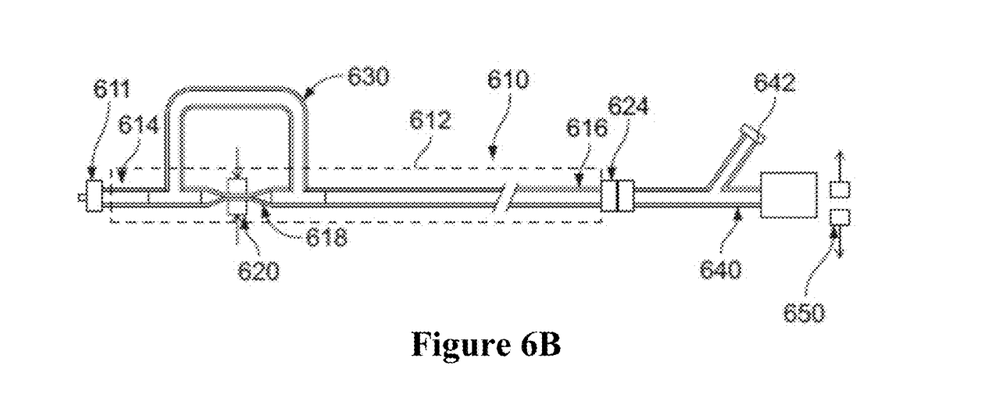

FIGS. 6A and 6B illustrate a catheter delivery device with an external clamp for use in delivery of a device catheter to a vessel of a patient with an external fluidic bypass. Device 600 may be used to carry out the methods 400 and 420 described in FIGS. 4A and 4B. Referring to FIGS. 6A and 6B, similar to catheter delivery device 500 of FIGS. 5A and 5B, a catheter delivery device 600 includes a hollow longitudinal body 610 with a clamping portion 612, an external fluidic bypass 630, and a hemostasis valve 640. The hollow longitudinal body 610 is configured to couple to a guide catheter (e.g., via attachment 611). The clamping portion 612 includes a distal end 614 coupled to the attachment 611, a proximal end 616 coupled to the hemostasis valve 640 (e.g., via attachment mechanism 624), and a guidewire securing section 618 that includes a clamp 620. In some cases, the hemostasis valve 640 includes pressure monitor port 642. It should be noted that FIG. 6A illustrates the clamp 620 is in the open position; in FIG. 6B, the clamp 620 is in the closed position.

In this embodiment, the catheter delivery device 600 further includes an external clamp 650. The external clamp 650 is used to secure the guidewire, for example, when the catheter reaches the guidewire securing section 618. As described above, the clamp 620 that secures the guidewire securing section 618 may be released (e.g., 410 of method 400) and/or placed in an open position when the catheter reaches the guidewire securing section 618. Therefore, instead of securing the guidewire with their hand while the device catheter is inserted the rest of the way into the patient's vessel, the external clamp 650 is used to secure the guidewire while the device catheter is inserted the rest of the way into the patient's vessel. As illustrated in FIG. 6A, clamp 620 is in the open position when external clamp 650 is in the closed position; and as illustrated in FIG. 6B, clamp 620 is in the closed position when external clamp 650 is in the open position, which supports the functionality described. Removal of the device catheter is similar to this process, just in reverse. By appropriate use of clamps 620 and 650, the guidewire can be secured against unintended movement during the insertion and/or removal process.

In some embodiments, a catheter delivery device may include hollow longitudinal body and a hemostasis valve with no fluidic bypass. This embodiment may be advantageous, for example, in situations in which there is not a blood pressure monitor coupled to the hemostasis valve. The hollow longitudinal body can include a guide catheter and a clamping portion. The guide catheter can include a distal end for access into a vessel of a patient and a proximal end coupled to a clamping portion. The clamping portion can include a distal end coupled to the guide catheter, a proximal end coupled to the hemostasis valve, and a guidewire securing section. In some cases, the guidewire securing section may include a clamp or have a clamp coupled to the guidewire securing section. In some cases, the catheter delivery device may include an external clamp to secure the guidewire when the guidewire securing section of the clamping portion is open. In some cases, the guidewire securing section is deformable. Indeed, the catheter delivery device may include any of the same features described above with respect to FIGS. 1A-3D and 5A-6B, but without the fluidic bypass. For example, the catheter delivery device with no fluidic bypass may include a pressure monitor port positioned distal from the clamping section, which allows for pressure monitoring even when the clamping section is clamping the guidewire.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A catheter delivery device having a catheter delivery guidewire clamp, comprising:
   a guide catheter having a distal end for access into a vessel of a patient and a proximal end coupled to a clamping portion;
   a hemostasis valve coupled to a proximal end of the clamping portion; and
   a tubular longitudinal body comprising:
     the clamping portion having a distal end coupled to the guide catheter and a guidewire securing section; and
     a fluidic bypass, wherein when the guidewire securing section of the clamping portion is securing a guidewire, the fluidic bypass maintains fluid communication between the guide catheter and the hemostasis valve, wherein the guidewire securing section and the fluidic bypass are separated by material that is attached along an entire length of an interior of the tubular longitudinal body.

2. The catheter delivery device of claim 1, further comprising a clamp coupled to the guidewire securing section.

3. The catheter delivery device of claim 1, wherein the guidewire securing section comprises a clamp.

4. The catheter delivery device of claim 3, further comprising an external clamp to secure the guidewire when the guidewire securing section of the clamping portion is open.

5. The catheter delivery device of claim 1, wherein the guidewire securing section is deformable.

6. The catheter delivery device of claim 5, wherein the guidewire is configured to be secured by a user pinching the guidewire securing section.

7. The catheter delivery device of claim 1, further comprising a pressure monitor port.

8. A catheter delivery guidewire clamp, comprising:
a tubular longitudinal body having a distal end, a proximal end, and a clamping portion, the clamping portion comprising a guidewire securing section, wherein the guidewire securing section comprises spring clamp, a vice clamp, a quick grip clamp, a power clamp, a trigger clamp, a screw clamp, a clip hanger clamp, a hose clamp, a Foerster clamp, a hemostatic clamp, or a valve; and
a fluidic bypass, wherein when the guidewire securing section of the clamping portion is securing a guidewire, the fluidic bypass maintains fluid communication between the distal end and the proximal end, wherein the guidewire securing section and the fluidic bypass are separated by material that is attached along an entire length of an interior of the tubular longitudinal body.

9. The catheter delivery guidewire clamp of claim 8, wherein the guidewire securing section is deformable.

10. The catheter delivery guidewire clamp of claim 9, wherein the guidewire is configured to be secured by a user pinching the guidewire securing section.

11. The catheter delivery guidewire clamp of claim 8, further comprising a guide catheter extending from the distal end of the tubular longitudinal body, wherein the proximal end of the tubular longitudinal body is configured to couple to a hemostasis valve.

12. The catheter delivery guidewire clamp of claim 8, further comprising a hemostasis valve extending from the proximal end of the tubular longitudinal body, wherein the distal end of the tubular longitudinal body is configured to couple to a guide catheter.

13. A method of using a catheter delivery device having a catheter delivery guidewire clamp, the method comprising:
inserting a distal end of a guide catheter of a catheter delivery device into a vessel of a patient, the catheter delivery device comprising:
a tubular longitudinal body comprising:
the guide catheter having the distal end accessing the vessel of the patient and a proximal end coupled to a clamping portion;
the clamping portion having a distal end coupled to the guide catheter, a proximal end coupled to a hemostasis valve, and a guidewire securing section comprising an external clamp that clamps an outer surface of the guidewire securing section;
a fluidic bypass, wherein when the guidewire securing section of the clamping portion is securing a guidewire, the fluidic bypass maintains fluid communication between the guide catheter and the hemostasis valve wherein the guidewire securing section and the fluidic bypass are separated by material that is attached along an entire length of an interior of the tubular longitudinal body; and
the hemostasis valve;
inserting the guidewire through the hemostasis valve and the tubular longitudinal body and into the vessel of the patient;
securing the guidewire by compressing the guidewire securing section of the clamping portion with the external clamp to a closed position;
inserting a device catheter through the hemostasis valve and into the tubular longitudinal body;
releasing the guidewire securing section of the clamping portion to an open position; and
inserting the device catheter into the vessel of the patient.

14. The method of claim 13, further comprising:
removing the device catheter from the vessel of the patient and into the tubular longitudinal body;
securing the guidewire by clamping the guidewire securing section of the clamping portion; and
removing the device catheter from the tubular longitudinal body and out of the hemostasis valve of the catheter delivery device.

* * * * *